United States Patent [19]

Grimes

[11] 4,210,510

[45] Jul. 1, 1980

[54] GAS SENSOR WITH CLOSELY WOUND TERMINATION SPRINGS

[75] Inventor: Donald A. Grimes, Findlay, Ohio

[73] Assignee: Bendix Autolite Corporation, Fostoria, Ohio

[21] Appl. No.: 60,448

[22] Filed: Jul. 25, 1979

[51] Int. Cl.$^2$ ............................................. G01N 27/46
[52] U.S. Cl. ................................................. 204/195 S
[58] Field of Search ................ 204/195 S, 195 R, 1 S; 123/119 E

[56] References Cited

U.S. PATENT DOCUMENTS

| 3,960,692 | 6/1976 | Weyl | 204/195 S |
| 4,019,974 | 4/1977 | Weyl | 204/195 S |
| 4,040,930 | 8/1977 | Dillon | 204/195 S |
| 4,111,778 | 9/1978 | Davis | 204/195 S |

Primary Examiner—T. M. Tufariello
Attorney, Agent, or Firm—William G. Kratz, Jr.; Raymond J. Eifler

[57] ABSTRACT

The helical compression spring which completes the electrical circuit between the interior surface of a tubular ion conductive solid electrolyte gas sensing element closed at one end, and an electrical terminal retained in spaced relation to the open end of the sensing element is close wound adjacent the end exposed to temperatures which would cause open coils of the spring to relax and has a compressed length sufficient to maintain a preselected minimum force against the terminal and sensing element over the full range of operating temperatures to which the sensor is exposed. In an alternate embodiment of the invention, this spring is provided with a closely wound portion at each end so that the sensor can be assembled by inserting the spring either end first.

7 Claims, 4 Drawing Figures

GAS SENSOR WITH CLOSELY WOUND TERMINATION SPRINGS

BACKGROUND OF THE INVENTION

1. Field of the Invention

This invention relates to sensors composed of ceramic and metallic parts which are subject to large variations in temperature. It has particular application to ion conductive solid electrolyte gas sensors used in detecting the oxygen concentration in the exhaust gases of an internal combustion engine.

2. Prior Art

U.S. Pat. No. 4,111,778 assigned to the assignee of the present invention, and the contents of which are incorporated by reference herein, discloses an oxygen gas sensor of the type in which one surface of an ion conductive solid electrolyte, such as zirconium dioxide, is exposed to a reference concentration of oxygen and an opposed surface is exposed to the oxygen concentration to be sensed. A difference in oxygen concentration on the two sides of the sensor element generates an electrical potential between the two surfaces which is representative of this difference in oxygen concentration. For use in analyzing or controlling the fuel/air ratio of a combustion engine gas mixture, the surface of the solid electrolyte can be coated with a catalyst so that the sensor will produce an electrical step function as the air/fuel ratio goes through stoichiometric from a rich mixture to a lean mixture.

As in many solid electrolyte sensors, the zirconium dioxide element in U.S. Pat. No. 4,111,778 is shaped in the form of a tube closed at one end and open at the other. The tube is mounted in a metallic shell which screws into the exhaust system of an internal combustion engine with the closed end of the tube disposed in the gas stream to be analyzed and the open end exposed to ambient air. A ventilated, metallic sleeve is provided over the open end of the tube to protect it from water and solid contaminants. Likewise, the closed end of the tube may be covered by a fluted, cup-shaped, metallic shield which protects the solid electrolyte from particulates in the gas stream.

Both the inside and outside surfaces of the solid electrolyte tube are coated with a porous layer of platinum or palladium which serves as a catalyst for the gases in contact therewith and as an electrode for the sensor. The coating on the outside of the tube is electrically connected to the metallic shell which serves as a ground terminal for the sensor. The coating on the inside of the tube is in electrical contact with a stud seated in a counterbore in the tube. A helical compression spring mounted on the stud bears against a metallic terminal axially retained by an insulator mounted in the end of the ventilated sleeve covering the open end of the tube to complete the electrical circuit between the interior surface of the tube and the terminal.

In addition to completing the electrical circuit for the internal surface of the sensing tube, the helical compression spring accommodates for movement of sensor parts with respect to each other resulting from thermal expansion. This is important because a sensor used in detecting the oxygen concentration in the exhaust gases of an internal combustion engine may be exposed to operating temperatures of from 300° up to 1000° Celsius. Furthermore, the temperature difference between the electrical terminal and the sensing tube could be very high when it is considered that the temperature of the sensor could be sub-zero before starting of the engine. If a uniformly wound compression spring with open coils is seated directly in the counterbore in the sensing element, the high operating temperatures will cause the portion of the spring in the counterbore area to relax, thereby impairing the electrical contact between the terminal and the internal surface of the sensing tube. The stud was used in the sensor disclosed in U.S. Pat. No. 4,111,778 to raise the spring out of the hotter area in the counterbore in order to alleviate this problem. The stud, however, is an expensive item to manufacture which, of course, raises the cost of the sensor.

Thus, it is a primary object of this invention to provide a solid electrolyte gas sensor which is reliable over the full range of operating temperatures to which it is exposed and can be produced as economically as possible.

Specifically, it is an object of this invention to provide such a sensor which accommodates for thermal expansion of the various components of the sensor while maintaining electrical continuity in the sensor circuits over the full thermal operating range.

More specifically, it is an object of this invention to provide a helical compression spring for such sensors which will maintain at least a minimum force against components of the internal sensor electrical circuit over the full thermal operating range.

SUMMARY OF THE INVENTION

In accordance with the invention, the helical compression spring (39) which completes the electrical circuit between the electrical conductor (7) on the inside of a closed tube type solid electrolyte gas sensing element (1) and an axially spaced terminal (43) has a closely wound portion (65) adjacent the end of the spring exposed to temperatures which would cause open coils of the spring to relax and has a compressed length sufficient to maintain at least a preselected force against the terminal (43) and the sensing element (1) over the range of operating temperatures to which the sensor components are exposed. In the preferred embodiment of the invention, the tightly wound portion (65) of the spring (39) extends into a counterbore in the sensing element (1). In addition, the closely wound end (65) of the spring should preferably be ground in a plane (67) transverse to the axis of the helix to provide more electrical contact surface. The other end of the spring should then be bent radially inward (69) in a plane transverse to the axis of the coil as a stop for the electrical wire (63) prior to its being crimped into the hollow terminal (43).

Alternatively, part of the closely wound portion of the helical compression spring can be located at each end (65a, 65b) of the spring (39') in which case the spring (39') can be inserted either end first during assembly. With this arrangement, the depth of the counterbore should be the same as the length of the closely wound portion and both ends of the spring (39') should be ground flat on a plane (67a, 67b) transverse to the axis of the helix.

To prevent damage to the coating (7) on the inside of the sensing element (1) and to made better electrical contact with the compression spring (39), the sensing tube (1) may be counterbored to form a shoulder (35). The spring (39) may then bear against an annular contact element (37) seated on the shoulder (35) and in electrical contact with the coating (7) which extends upward over the shoulder (35).

With the present invention, sufficient force is maintained by the helical compression spring (39) against the sensing element (1) and the terminal (43) such that good electrical continuity is maintained throughout the operating range of the sensor. These results are achieved while at the same time a costly part in prior art sensors is eliminated. In addition, by making the ends of the spring symmetrical so that either end may be inserted first, assembly time is reduced resulting in additional cost savings.

DESCRIPTION OF THE PREFERRED EMBODIMENT

Figure 1:
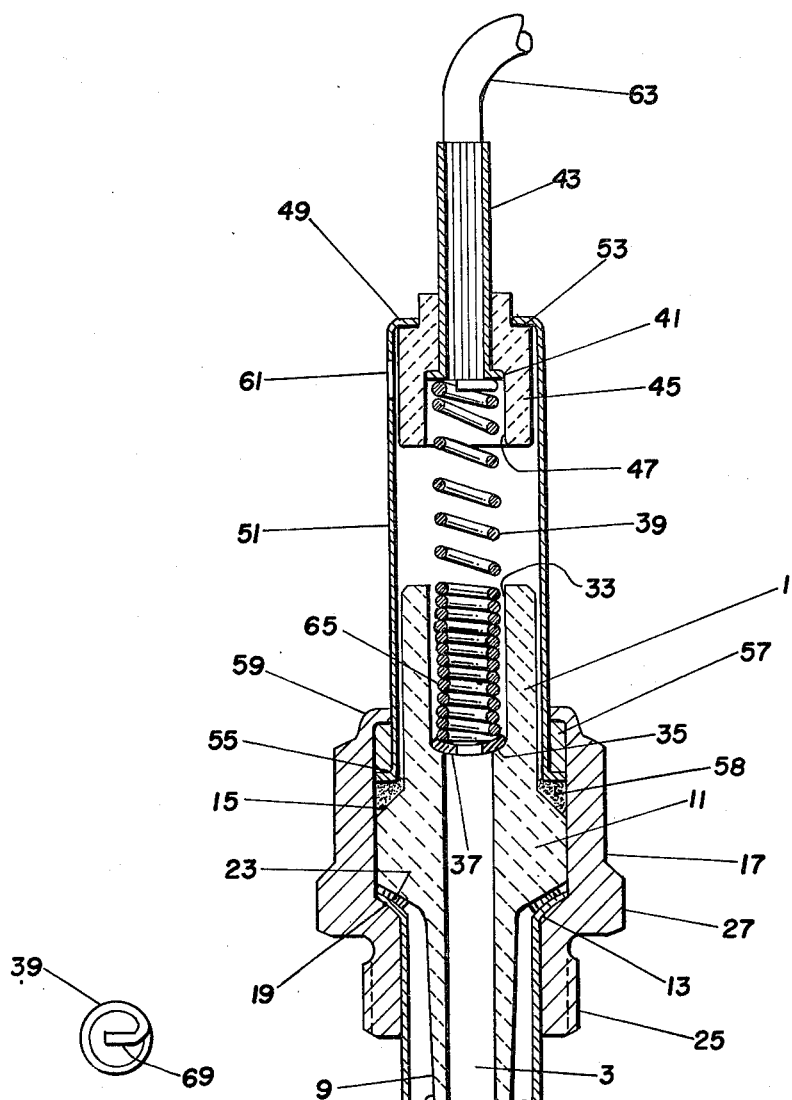
FIG. 1 is a longitudinal sectional view through a sensor incorporating the present invention.

As shown in FIG. 1, the gas sensor includes a tubular sensing element 1 made of an ion conductive solid electrolyte material such as zirconium dioxide. The tube 1 has a bore 3 which is closed at one end 5 and open at the other. Both the interior surface 7 and the exterior surface 9 of the tubular sensing element 1 are coated with a porous layer of platinum or palladium which serves as a catalyst for the gases exposed to the surfaces and as an electrode for the sensor. A radially enlarged portion 11 near the longitudinal center of the tubular sensing element 1 forms a pair of annular shoulders 13 and 15.

The tubular sensing element 1 is mounted in an annular metallic shell 17 having an internal shoulder 19 which bears against the shoulder 13 on the sensing element 1 through the flared end of a metallic shield 21 and an electrically conductive washer 23. The metallic shell 17 has a threaded portion 25 adapted to be threaded into a bore in the wall of the manifold or exhaust system of an internal combustion engine by a wrench applied to a hexagonal section 27. The sensor is installed with the closed end 5 of the tube projecting into the exhaust system. The shield 21 is fluted as at 29 to prevent direct impingement of particulates in the gas stream on the sensing element. The shield may also have apertures 31 on the bottom through which the gases may escape.

The open end of the tubular sensing element 1 is counterbored as at 33 and the platinum coating on the interior surface 7 of the tube extends upward over the shoulder 35 formed by the counterbore. An electrically conductive annular contact element 37 is seated on the shoulder 35 in electrical contact with the platinum coating. An electrically conductive, helical compression spring 39 is inserted in the counterbore 33 and bears against the annular contact element 37. The other end of the spring 39 bears against a flange 41 on the bottom of a hollow terminal 43. The terminal 43 extends axially through an annular electrical insulator 45 with the flange 41 urged by the spring 39 against a shoulder in the insulator formed by a counterbore 47.

The insulator 45 is retained in spaced relation to the sensing element 1 by a radial inwardly directed flange 49 on one end of a metallic sleeve 51 which bears against an annular shoulder 53 on the end of the insulator. A radial outwardly directed flange 55 on the other end of the metallic sleeve 51 is received in the annular gap between the sensing element 1 and the metallic shell 17. A spacer ring 57 is placed over the flange 55 and the edge 59 of the metallic shell 17 is crimped over on the spacer ring to hold the sensor together as a unit and to compact a ring of talc 58 between the flange 55 on the sleeve 51 and the shoulder 15 on the sensing element. This ring of talc 58 provides a fluid tight seal to prevent exhaust gases from escaping toward the open end of the sensing tube 1.

The sleeve 51 is provided with aperatures 61 adjacent the insulator 45 which allow ambient air to enter the sleeve and through the annular contact element 37 to come in contact with the catalytic coating on the interior surface 7 of the sensing element 1. As disclosed in U.S. Pat. No. 4,111,778, the aperatures 61 may be partially covered with a protective clip (not shown) to prevent water and other contaminants from being introduced into the interior of the sensor.

Electrical connections for the sensor are provided by an insulated electrical lead 63 which is inserted in the hollow terminal 43 and by the metallic shell 17 which provides a ground terminal through the chassis. The lead 63 is electrically connected to the coating on the interior surface 7 of the sensing element 1 through the terminal 43, the helical compression spring 39 and the annular contact element 37, while the shell 17 is electrically connected to the sensing exterior surface 9 through electrically conductive washer 23 and the shield 21. As disclosed in U.S. Pat. No. 4,111,778, a separate grounding wire can be connected to the metallic sleeve 51 to provide an additional ground connection.

In operation, the sensor is screwed into a threaded opening in the wall of an internal combustion engine exhaust system with the shielded tube protruding into the exhaust gas stream. With the exterior surface 9 of the sensing element 1 thus exposed to the exhaust gases and the interior surface 7 exposed to ambient air, a potential is generated on lead 63 which is a function of the partial pressure of oxygen present in the exhaust gases. As taught by the prior art, this signal may be used for regulating the air/fuel ratio of the engine.

As noted above, the sensing element 1 is made of zirconium dioxide while the shell and the sleeve 51 are made of steel. Under operating conditions, these parts can be exposed to operating temperatures of up to 1000° Celsius. When not operating, the parts may be exposed to sub-freezing temperatures. The thermal expansion for these materials produces considerable variation in the dimensions of the parts over this range of temperatures. It is for this reason that a spring has been used to complete the circuit between the sensing element and the terminal 43. However, the spring must exert a certain minimum force against these parts in order to maintain low resistance electrical contact without providing fixed connections. It has been found that at the higher operating temperatures to which the sensor may be exposed, the hot portions of the spring tend to relax thereby increasing the resistance of the electrical connections between the sensing element and the terminal with an adverse effect on the accuracy of the determination of the partial pressure of oxygen in the exhaust gas.

Figure 3:
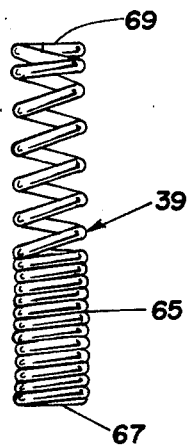
FIG. 3 is an end view of one end of the spring shown in FIG. 2.
Figures 2, 4:
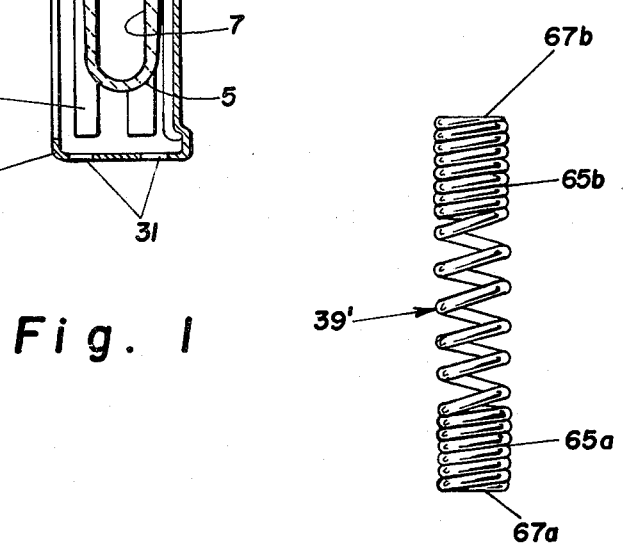
FIG. 2 is a side view of the helical compression spring made in accordance with one embodiment of the invention.
FIG. 4 is a side view of a helical compression spring made in accordance with another embodiment of the invention.

In order to overcome this tendency for the spring 39 to relax at high operating temperatures, the spring 39 has been wound tightly as shown in FIG. 2 at the end 65 which is exposed to high temperature with this closely wound portion of the spring inserted in the counterbore 33 in the sensing element 1 as shown in FIG. 1, the open coils of the spring remain cool enough so that the spring can maintain at least a preselected minimum force against the other components over the full operating range of the sensor. As an example, using 0.050 inch diameter ES-540 stainless steel wire, a coil 0.250 inches in outside diameter with a tightly wound portion 65, 0.50 inches in length and a free length of 0.86 inches for an overall length of 1.36 inches was wound to produce a spring rated at 100 pounds per inch of compression. After stress relieving, the spring generated a force of from 10.5 to 15.5 pounds when compressed to a length of 1.23 inches which is the nominal compressed length of the spring when installed in the sensor. The closely wound end 67 was ground flat on a plane transverse to the axis of the helix for better electrical contact and the free end 69 (FIG. 3) was bent radially inward in a plane transverse to the axis of the helix to serve as a stop for the lead 63 which is inserted in the hollow terminal 43.

Alternatively, as shown in FIG. 4, the spring 39' can be closely wound for 0.25 inches at each end at 65a and b with 0.86 inches of free length inbetween. Both ends of this spring 67 a and b may be ground flat as previously described. The advantage of this form of spring is that it can be inserted in the bore of the sensing element 1 either end first during assembly. The remaining dimensions and the force generated are the same as with the previously described spring. This alternate spring would be used with a sensing element 1 having a shorter upper section such that the counterbore 33 is only 0.250 iches deep.

Both embodiments of the invention disclosed provide a sensor in which the helical compression spring provides good electrical contact with the sensing element and the terminal throughout the full operating temperature range of the sensor.

What is claimed is:

1. An electrochemical gas sensor comprising:

An ion conductive solid electrolyte sensing element in the form of a tube closed at one end and open at the other end, a first electrical conductor on the interior surface of said sensing element, a second electrical conductor on the exterior surface of said sensing element, a tubular sleeve fitted over and extending beyond the open end of the sensing element and secured thereto, an insulator axially retained by said sleeve in spaced relation to said open end of the sensing element, an elongated electrical terminal retained in axial alignment with said sleeve by said insulator and electrically insulated from said sleeve thereby, said terminal extending through said insulator, and an electrically conductive, helical compression spring extending axially through said sleeve and compressed between said terminal and said sensing element, said spring forming a portion of a series electrical circuit between the first electrical conductor on the interior surface of said sensing element and said terminal; said spring having a tightly wound portion adjacent the end of the spring exposed to temperatures which would cause open coils of the spring to relax and having a compressed length sufficient to maintain at least a preselected force against the terminal and the sensing element over the range of operating temperatures to which the sensor components are exposed.

2. The sensor of claim 1 wherein the tighty wound portion of the helical compression spring is located at the end adjacent to the sensing element.

3. The sensor of claim 1 wherein the end of the wire forming the helical compression spring adjacent to said terminal is bent radially inward across the center of the helix in a plane transverse to the axis thereof to provide a stop for the electrical lead which is inserted into the terminal.

4. The sensor of claims 2 or 3 wherein the tightly wound end of the helical compression spring is ground on a plane transverse to the axis of the helix to provide improved contact area at that end of the spring.

5. The sensor of claim 1 wherein the helical compression spring includes a tightly wound portion at each end thereof.

6. The sensor of claim 5 wherein both tightly wound ends of said helical compression spring are ground on a plane transverse to the axis of the helix to provide improved contact area at both ends of the spring.

7. The sensor of claims 2 or 5 wherein the bore in the open end of the tubular sensing element is counterbored to form a shoulder with said first electrical conductor on the interior surface of said sensing element extending up over said shoulder, and including an electrically conductive annular contact element which seats on said shoulder and makes electrical contact with said first electrical conductor, while said helical compression spring bears against said contact element to complete the electrical circuit between the first conductor on the interior of said tubular sensing element and said terminal.

* * * * *